United States Patent [19]

Bullard

[11] Patent Number: 5,791,341
[45] Date of Patent: Aug. 11, 1998

[54] OROPHARYNGEAL STENT WITH LARYNGEAL ADITUS SHIELD AND NASAL AIRWAY WITH LARYNGEAL ADITUS SHIELD

[76] Inventor: James Roger Bullard, P.O. Box 14727, Augusta, Ga. 30919-0727

[21] Appl. No.: 768,805

[22] Filed: Dec. 18, 1996

Related U.S. Application Data

[60] Provisional application No. 60/008,872 Dec. 19, 1995.

[51] Int. Cl.$^6$ ................................................ A61M 16/00
[52] U.S. Cl. ........................... 128/207.15; 128/200.26; 128/207.18
[58] Field of Search ................... 128/200.26, 207.14, 128/207.15, 207.18, DIG. 26; 604/96, 174

[56] References Cited

U.S. PATENT DOCUMENTS

| | | | |
|---|---|---|---|
| 2,463,149 | 3/1949 | Caine | 128/200.26 |
| 2,541,402 | 2/1951 | Caine | 128/200.26 |
| 3,734,100 | 5/1973 | Walker et al. | 128/207.15 |
| 3,915,173 | 10/1975 | Brekke | 128/207.18 |
| 4,150,676 | 4/1979 | Jackson | 128/207.18 |
| 4,231,365 | 11/1980 | Scarberry | 128/207.15 |
| 4,235,239 | 11/1980 | Elam | 128/207.15 |
| 4,471,776 | 9/1984 | Cox . | |
| 4,502,482 | 3/1985 | DeLuccia et al. | 128/207.15 |
| 4,509,514 | 4/1985 | Brain | 128/207.15 |
| 4,538,606 | 9/1985 | Whited | 128/207.15 |
| 4,565,194 | 1/1986 | Weerda et al. . | |
| 4,688,568 | 8/1987 | Frass et al. | 128/207.15 |
| 4,791,923 | 12/1988 | Shapiro . | |
| 4,819,619 | 4/1989 | Augustine et al. | 128/200.26 |
| 4,960,122 | 10/1990 | Mizus | 128/207.14 |
| 5,241,956 | 9/1993 | Brain . | |
| 5,303,697 | 4/1994 | Brain | 128/200.26 |
| 5,339,805 | 8/1994 | Parker | 128/200.26 |
| 5,443,063 | 8/1995 | Greenberg | 128/207.15 |
| 5,499,625 | 3/1996 | Frass et al. . | |
| 5,513,627 | 5/1996 | Flam | 128/200.26 |

FOREIGN PATENT DOCUMENTS

| | | | |
|---|---|---|---|
| 0 448 878 | 10/1991 | European Pat. Off. | 128/207.15 |
| 0 712 638 A1 | 5/1996 | European Pat. Off. . | |
| 2 225 955 A | 6/1990 | United Kingdom . | |
| WO95/32754 | 12/1995 | WIPO . | |

*Primary Examiner*—Mickey Yu
*Assistant Examiner*—Virendra Srivastava
*Attorney, Agent, or Firm*—St. Onge Steward Johnston & Reens

[57] ABSTRACT

An oropharyngeal stent and aditus shield comprises a curved flexible tubular body containing a central airway with a first inflatable cuff surrounding a portion of the body, and a laryngeal aditus shield comprising a generally triangular second inflatable cuff located at the distal end of the body. In a nasal airway embodiment, the airway comprises a body with a laryngeal aditus shield.

4 Claims, 10 Drawing Sheets

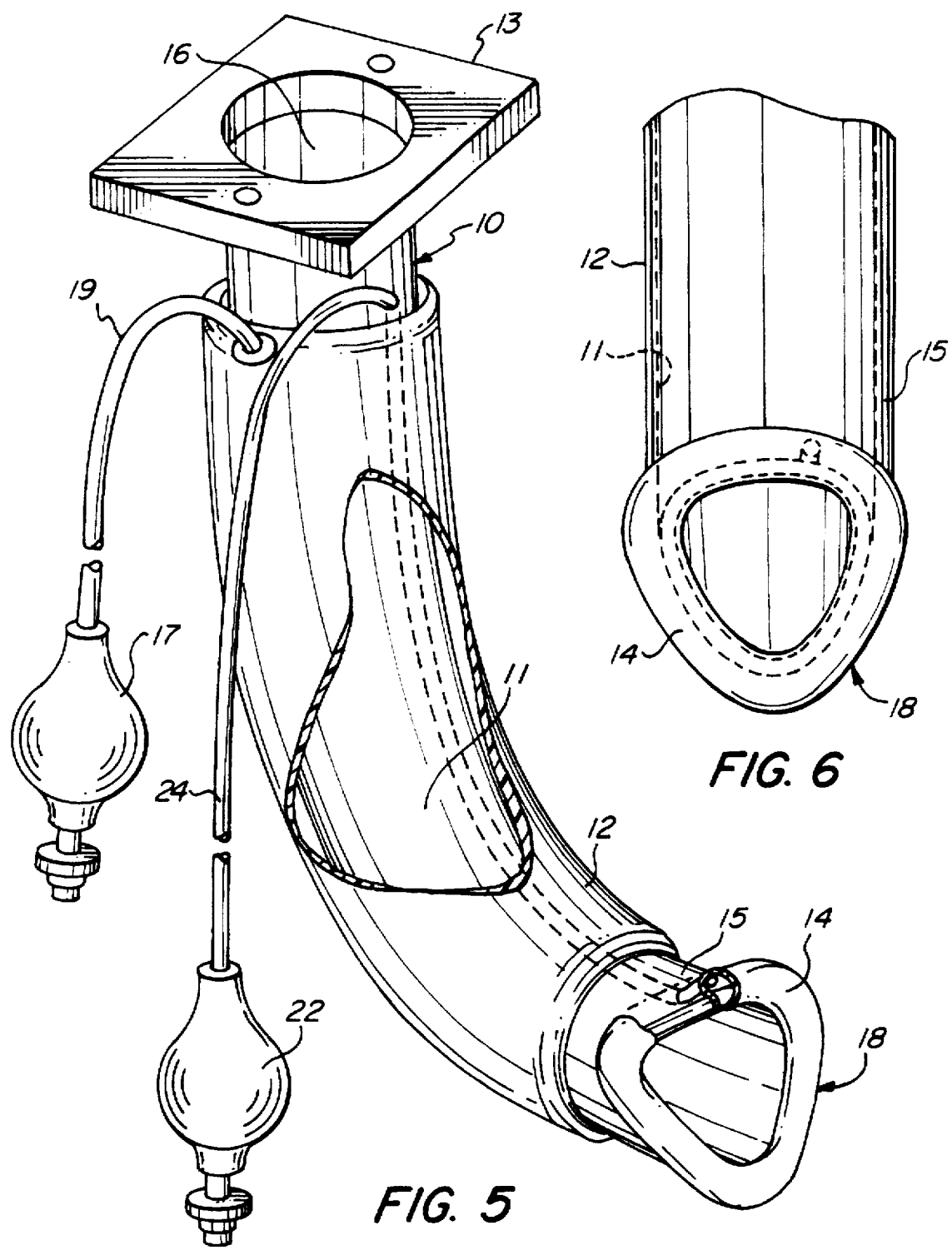

OROPHARYNGEAL STENT WITH LARYNGEAL ADITUS SHIELD AND NASAL AIRWAY WITH LARYNGEAL ADITUS SHIELD

This application is based on, and I claim priority rights under 35 U.S.C. §119(e) from, U.S. Provisional patent application Ser. No. 60/008,872, filed Dec. 19, 1995.

SPECIFICATION

FIELD OF THE INVENTION

The present invention relates generally to medical devices for patient ventilation and anesthetic administration during surgery.

BACKGROUND OF THE INVENTION

The conventional oropharyngeal airway is designed primarily to elevate the tongue during induction of anesthesia. However, this does not completely resolve an obstructed airway in many cases. When the patient is in the supine position during induction and/or maintenance of anesthesia, not only does the tongue and epiglottis impinge on the posterior pharyngeal wall, but the lateral tissues of the oral pharynx (e.g. the soft palate) tend to intrude on the patency of the airway. This is most commonly seen in those patients that are edentulous and obese, but may be encountered in unsuspected cases. This problem greatly contributes to that class of patients commonly referred to as "difficult to ventilate".

Laryngeal mask airways (LMAs), such as disclosed in Brain, U.S. Pat. Nos. 4,995,388 and 5,241,956, have begun to be in common use. However, such LMAs have recently been reported to be contraindicated where a Mallampati classification indicates a difficult ventilation classification. Among the problems associated with LMAs are difficulties of blind tracheal intubation, suboptimal seating of the LMA and consequent gas leak around the LMA, inadequate airway, and, in cases where the patient is insufficiently anesthetized, the triggering of reflexes including regurgitation, and consequent risk of aspiration of vomitus. LMAs are also contraindicated where the patient suffers edema, peripharyngeal, and pharyngeal abscesses, bleeding and/or disruption of the mucosa, because the LMA may aggravate edema.

In such cases, other methods of airway management may be attempted. Both oral and nasal airways may be attempted, also exaggerated mandible retraction and/or head extension, four-handed ventilation techniques, and attempts at visualization and intubation of the trachea. Many times these attempts are unsuccessful and further compromise the airway by trauma, bleeding and an increase of secretions. Also, repeat doses of muscle relaxing drugs compound the problem of impingement of lateral tissues of the oral pharynx on the airway.

In an effort to avoid this dilemma, a new and different airway is proposed.

SUMMARY OF THE INVENTION

It is an object of the invention to provide an airway or stent with a laryngeal aditus shield that will be useful even in the difficult airway situations described above, and which avoids problems associated with conventional LMAs.

These objects, and other objects as disclosed in this application, are achieved by an oropharyngeal stent and laryngeal aditus shield, and a nasal airway and laryngeal aditus shield, as described below.

The present application describes a new airway or stent that is suitable for patients with difficult pathology problems in the pharynx, and that can be established with minimal need for manipulation of the head and jaw that may complicate spinal/cervical injuries and which can be used with less than a deep anesthesia.

The oropharyngeal stent embodiment of this invention, while similar in shape to a conventional oropharyngeal airway, has the capability of supporting the soft tissues of the upper oral pharynx as well as providing a conduit for ventilation and intubation. This is achieved by incorporating a first inflatable cuff attached to the circumference of the new oropharyngeal stent. After this stent is placed in the usual manner (the stent being passed over a tongue retractor), this first cuff is inflated until satisfactory exchange occurs. The degree of inflation of the cuff will depend upon the size of the patient.

In addition to supporting the soft tissues, the distal opening of the oropharyngeal stent is provided with a laryngeal aditus shield comprising a second inflatable cuff. The laryngeal aditus shield when inflated will tend to envelop the vestibule of the larynx, extending from the epiglottis down to the arytenoids, but not to a level low enough to cause incompetence of the upper esophageal constrictor (a problem that can arise with LMAs and conventional oral airways if the patient is insufficiently anesthetized). The laryngeal aditus shield also directs gas flow towards the glottis and away from the esophagus thereby lessening the likelihood of gastric distension.

This oropharyngeal stent may be used to advantage in the field to safely secure the patient's airway in cases of upper airway trauma. Not only would a passage for gas exchange be provided, but the pressure of the large first cuff will help to tamponade the bleeding that could be present.

In a nasal airway embodiment, a nasal airway is provided with a laryngeal aditus shield comprising an inflatable cuff as in the oropharyngeal stent embodiment.

Other objects, aspects and features of the present invention in addition to those mentioned above will be pointed out in detail or will be understood from the following detailed description provided in conjunction with the accompanying drawings.

BRIEF DESCRIPTION OF THE DRAWINGS

The foregoing aspects and other features of the invention are explained in the following description, taken in connection with the accompanying drawings, wherein:

FIG. 5 is a perspective/cutaway view of an oropharyngeal stent and laryngeal aditus shield in accordance with another embodiment of the invention.

FIG. 6 is a front elevation view of a distal end of the oropharyngeal stent and laryngeal aditus shield of FIG. 5.

DETAILED DESCRIPTION OF THE INVENTION

Figure 1:
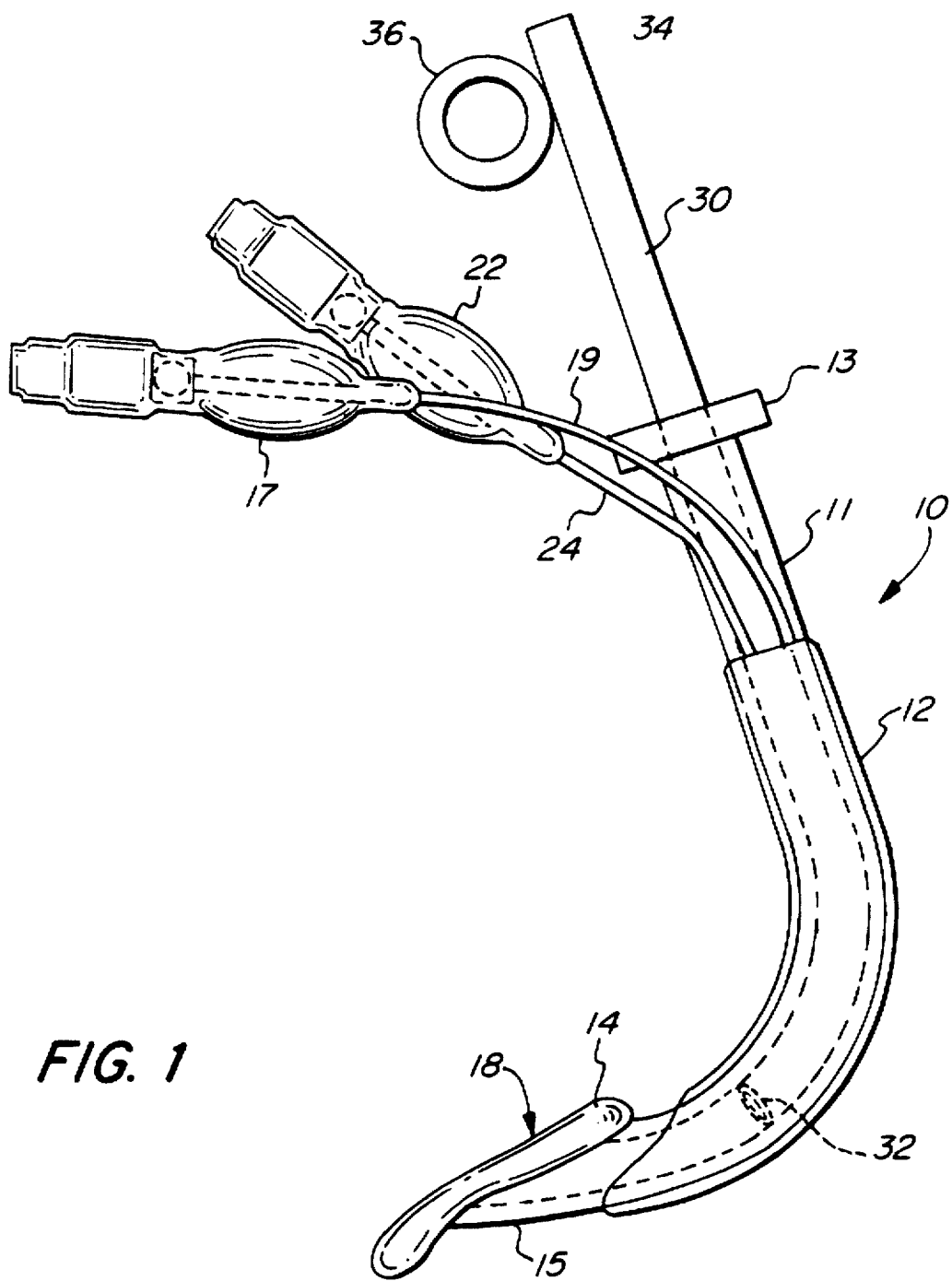
FIG. 1 is a side elevation view with partial cutaway view showing an oropharyngeal stent and laryngeal aditus shield with introducer and with cuffs deflated in accordance with one embodiment of the invention.
Figure 2:
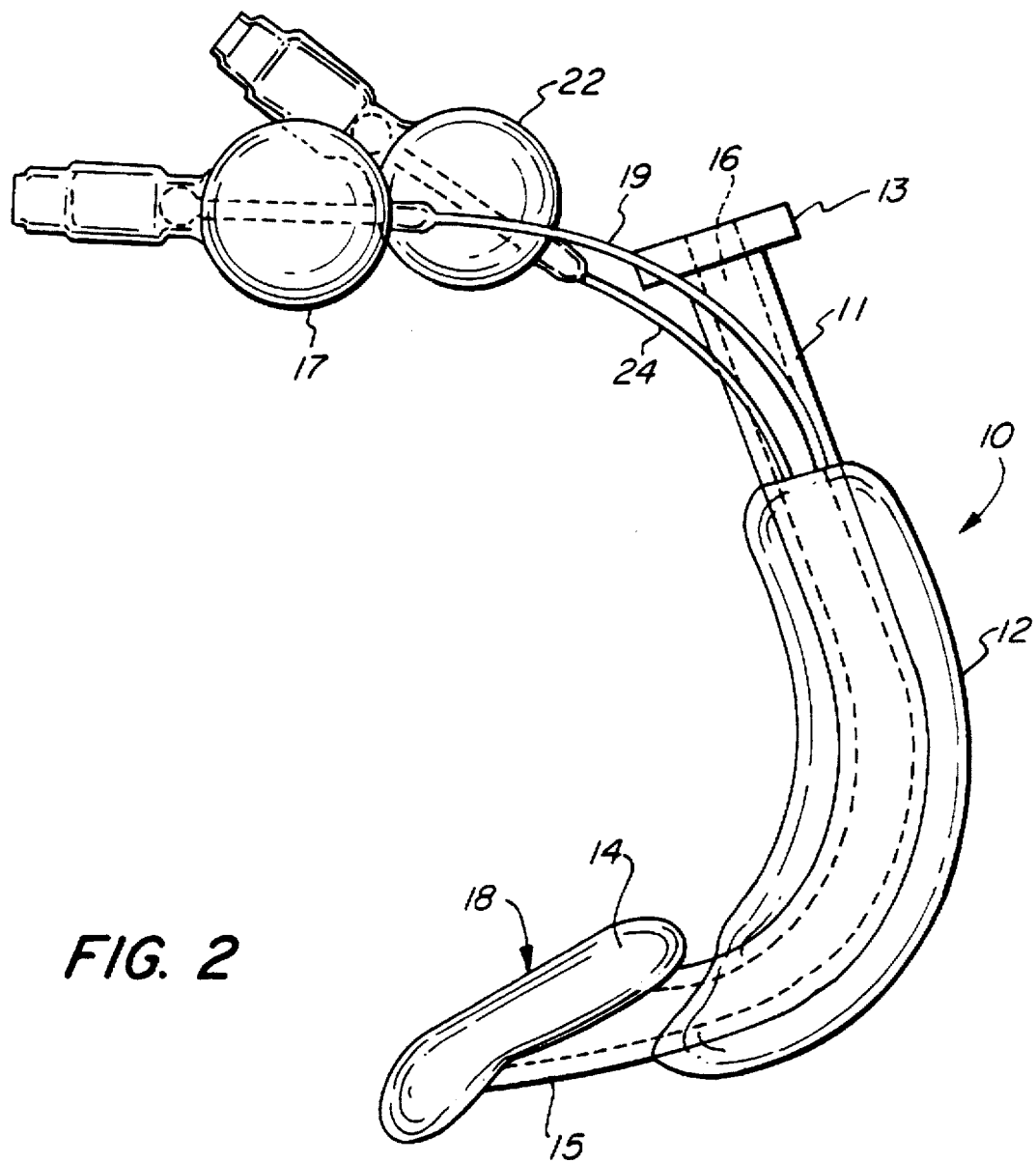
FIG. 2 is a side elevation view with partial cutaway view showing the oropharyngeal stent and laryngeal aditus shield of FIG. 1 without an introducer and with cuffs inflated.
Figure 3:
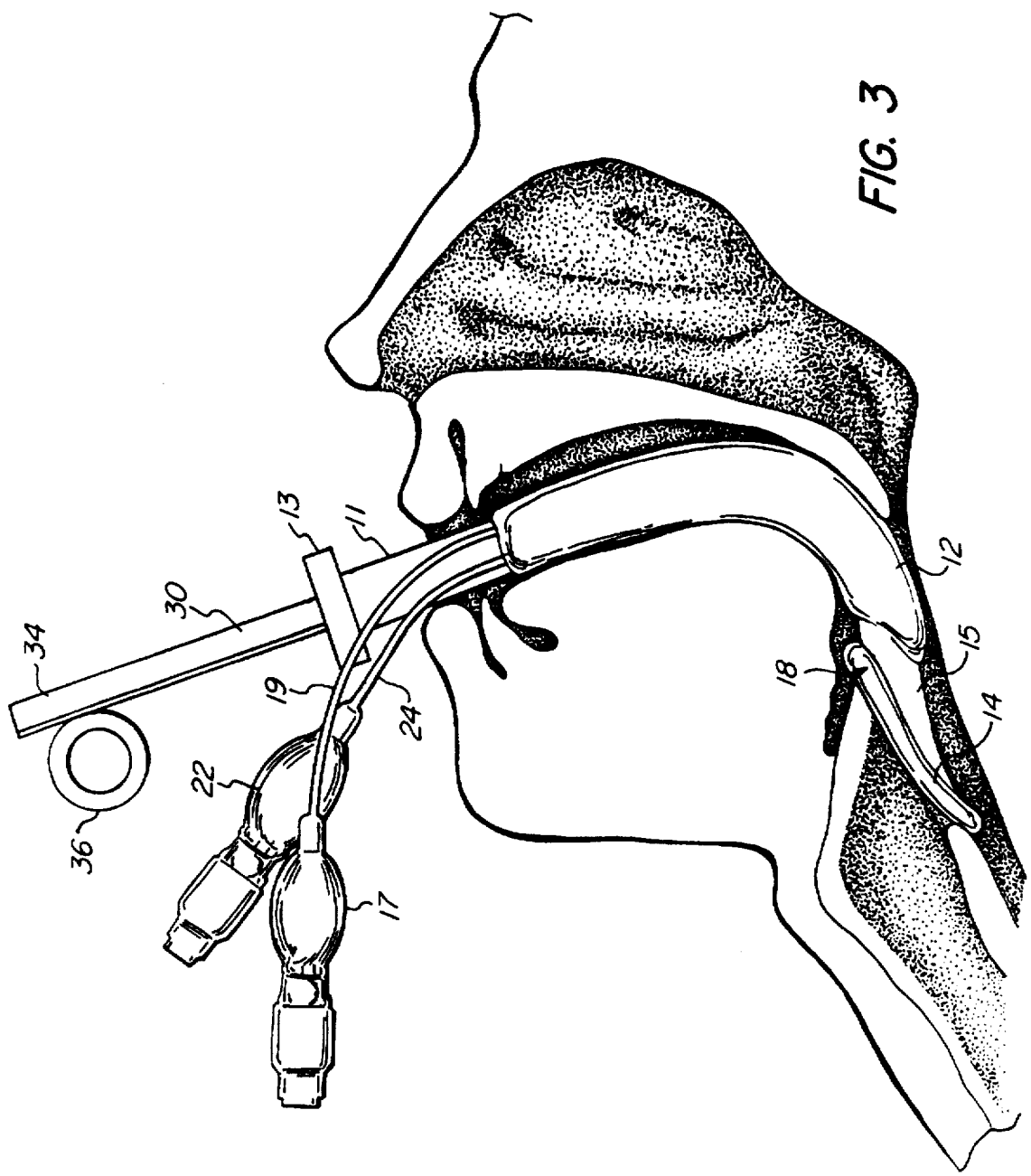
FIG. 3 is a side elevation view with partial cutaway view showing the oropharyngeal stent and laryngeal aditus shield of FIG. 1 introduced into a patient.
Figure 4:
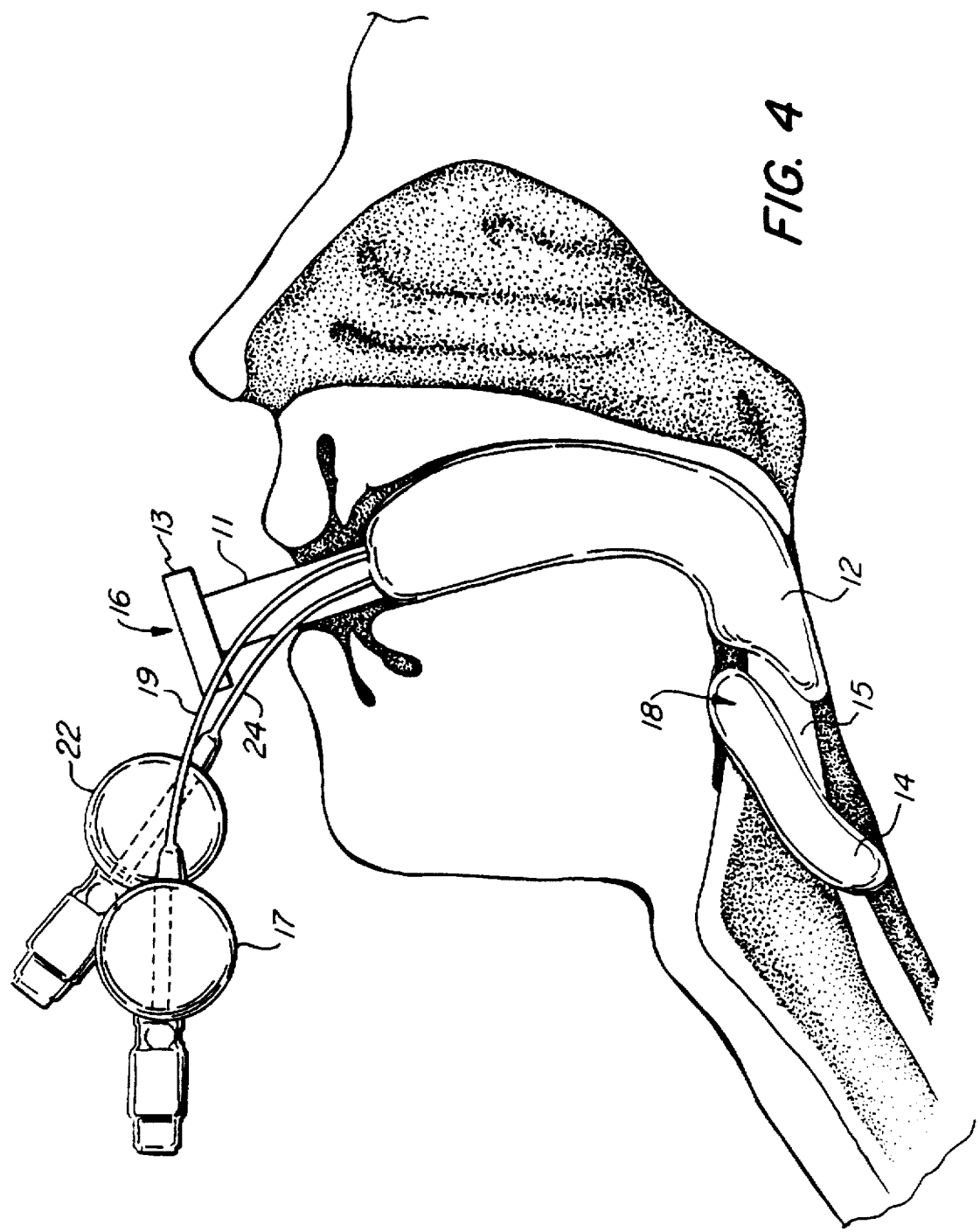
FIG. 4 is a side elevation view with partial cutaway view showing the oropharyngeal stent and laryngeal aditus shield of FIG. 2 introduced into a patient.

Referring to the attached FIGS. 1–7 and 10, an oropharyngeal stent 10 in accordance with the invention includes a body 11 curved in shape to conform to the normal anatomy of the human pharynx. Body 11 extends from the larynx to the mouth. Body 11 contains a central airway 16 and a proximal end 13 and a distal end 15. Body 11 is preferably generally oval in cross-sectional shape to provide an anatomically correct cross-section to avoid pressure on tissue unless provided by the cuff 12. The airway 16 is large enough to permit passage of an endotracheal tube within it. Body 11 is preferably formed of a relatively soft, flexible and pliable plastic material.

Attached to body 11 is a first inflatable cuff 12. Cuff 12 surrounds body 11 from near its proximal end to near the distal end. Cuff 12 is located so as not to contact the epiglottis when the stent 10 is established. Cuff 12 is inflatable via the inflating tubes, which are preferably incorporated in the wall of the stent 10. Cuff 12 is normally deflated during insertion of the stent 10 in a patient's pharynx, but is then inflated to establish the stent 10 and to prevent it from movement. The inflated cuff 12 provides a therapeutic tamponade effect to reduce bleeding. More significantly, it locates the stent 10 in the pharynx without creating the risk of rupturing diseased or pathological tissue that can arise from other intubation methods. Means for inflating the cuff 12 are provided and preferably includes a conventional valved pilot balloon 17 and assorted tubing 19. Other means may be provided that incorporate the necessary valving and provides low pressure air or nitrogen to inflate cuff 12.

Figure 7:
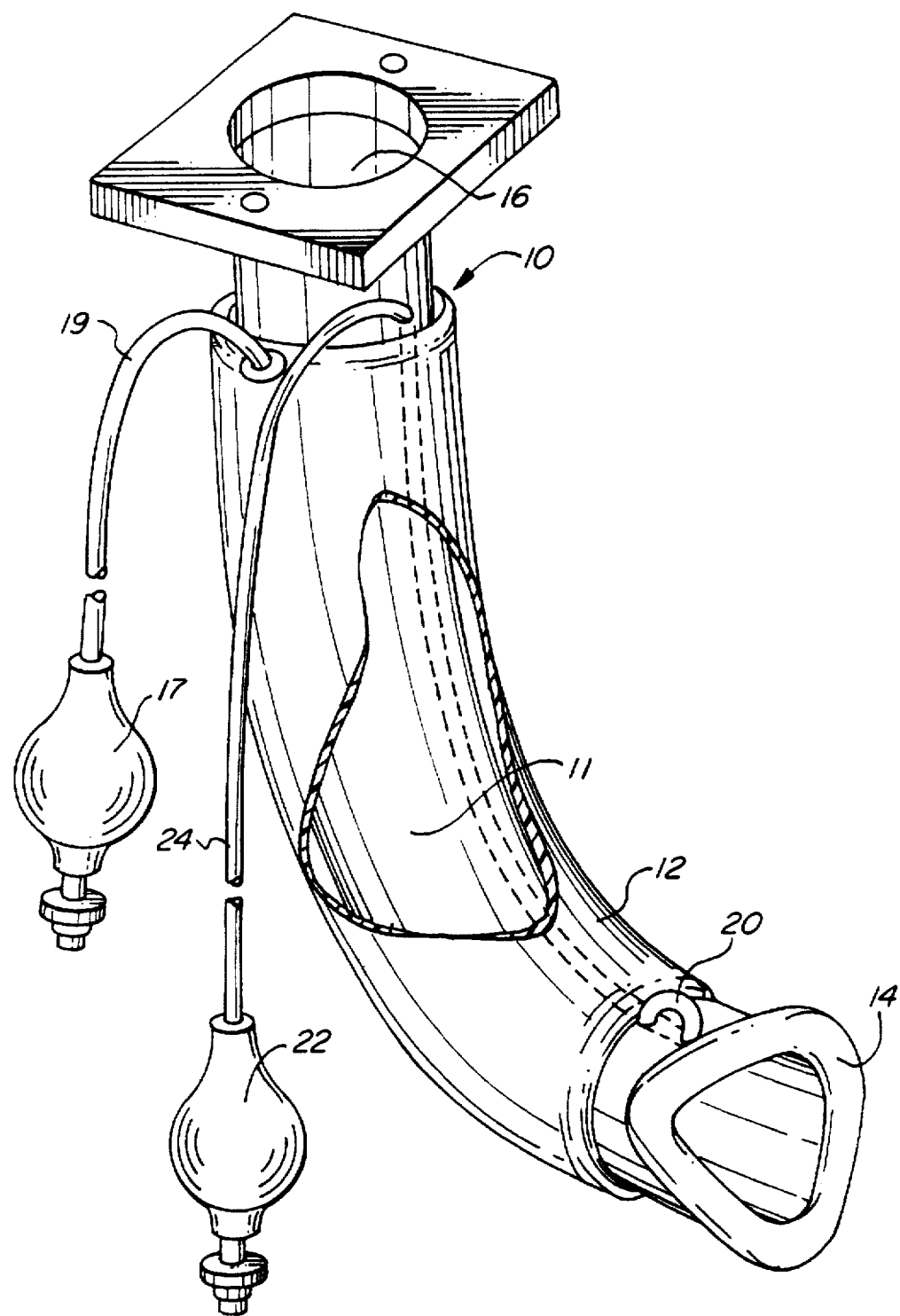
FIG. 7 is a perspective/cutaway view of the oropharyngeal stent of FIG. 5 with an anterior loop.

At the distal end 15 of body 11 is provided a laryngeal aditus shield 18, which serves, when inflated, to seal the area around the larynx. The laryngeal aditus shield 18 comprises a second inflatable cuff 14. Second cuff 14 is shaped to conform to the cross-sectional shape of the vestibule of the larynx, i.e., it is generally triangular/cardioid in shape, as shown in FIGS. 5–7. As used herein, the term "triangular" with reference to the second cuff means a triangular shape, with straight or curved side walls, and preferably with rounded corners as illustrated in the Figures and includes cardioid shapes. Preferably, the distal end of the body 11 is also triangular (as defined above) in cross-sectional shape. The second inflatable cuff 14 serves the function of a laryngeal mask to seal the larynx to provide effective ventilation. The second cuff 14 is thinner and narrower than the donut shaped cuff of a conventional LMA. The second cuff 14 is sized to fill the area above the vocal cords but not to overflow into the hypopharynx which could cause incompetence of the inferior constriction of the pharynx. Means for inflating the second cuff 14 are provided and preferably includes a conventional valved pilot balloon 22 and tubing 24. Other means may be provided that incorporates the necessary valving and low pressure air or nitrogen to inflate cuff 14.

The body 11 may also have an anterior loop 20 at its distal end between said first and second cuffs 12 and 14. Loop 20 is located so that when the oropharyngeal stent 10 is introduced into a patient, the loop 20 slips over the epiglottis and rests in the valleculae to prevent displacement or advancement of the body 11 below the vocal cords.

An introducer may be used to assist in placing the stent 10 in the patient. Introducer 30 is preferably a hollow plastic tube shaped like the stent 10 to conform to the normal human anatomy of the pharynx. The introducer 30 has some flexibility but is relatively stiff to maintain its shape. The introducer 30 has a length slightly longer than that of the stent 10. The distal end 32 of the introducer is intended to be near or coextensive with the distal end 15 of the body 11 of the stent 10, but the proximal end 34 of introducer 30 extends about 4–5 inches (12.5 cm) beyond the proximal end 13 of the stent 10. The proximal end 34 of the introducer has a ring 36 to receive the thumb of the surgeon or anesthetist to permit better control of the introducer 30 as it is located in a patient.

The method of providing a patent airway includes introduction of the stent 10 with or without using the introducer 30. When the introducer 30 is to be used, the method comprises locating the introducer 30 inside of stent 10, with the cuffs deflated and compressed around the stent 10. The introducer 30 and stent 10 are inserted into the patient in the same way as done with a Bullard laryngoscope. The patient's head is in the neutral position and the neck is not extended. The patient's mouth is opened, but not widely (no more than 6 mm). After the introducer and stent are fully inserted (the introducer 30 orients the stent 10 to the laryngeal vestibule), the cuffs are inflated to free the introducer which can then be withdrawn. The inflated cuffs provide a pressure on the surrounding human tissue to provide a clear airway in the patient. The hollow introducer can also be used to provide suction as it is introduced into the patient and/or for the administration of a local anesthetic. The method without use of an introducer is substantially similar.

The oropharyngeal stent also facilitates the use of a flexible directable bronchoscope. After satisfactory ventilation is assured, the flexible directable bronchoscope, having been previously threaded through a small diameter endotracheal tube (6 to 6.5 mm), is passed through the new stent until the glottis is visualized. The flexible directable bronchoscope is then passed through the glottis into the upper trachea and the endotracheal tube is advanced into the trachea and positioned. The oropharyngeal stent is then deflated and stays in place just as an oropharyngeal airway is used today. However, the oropharyngeal stent surrounds the endotracheal tube and provides additional protection from dislodgement and damage secondary to biting.

Figure 10:
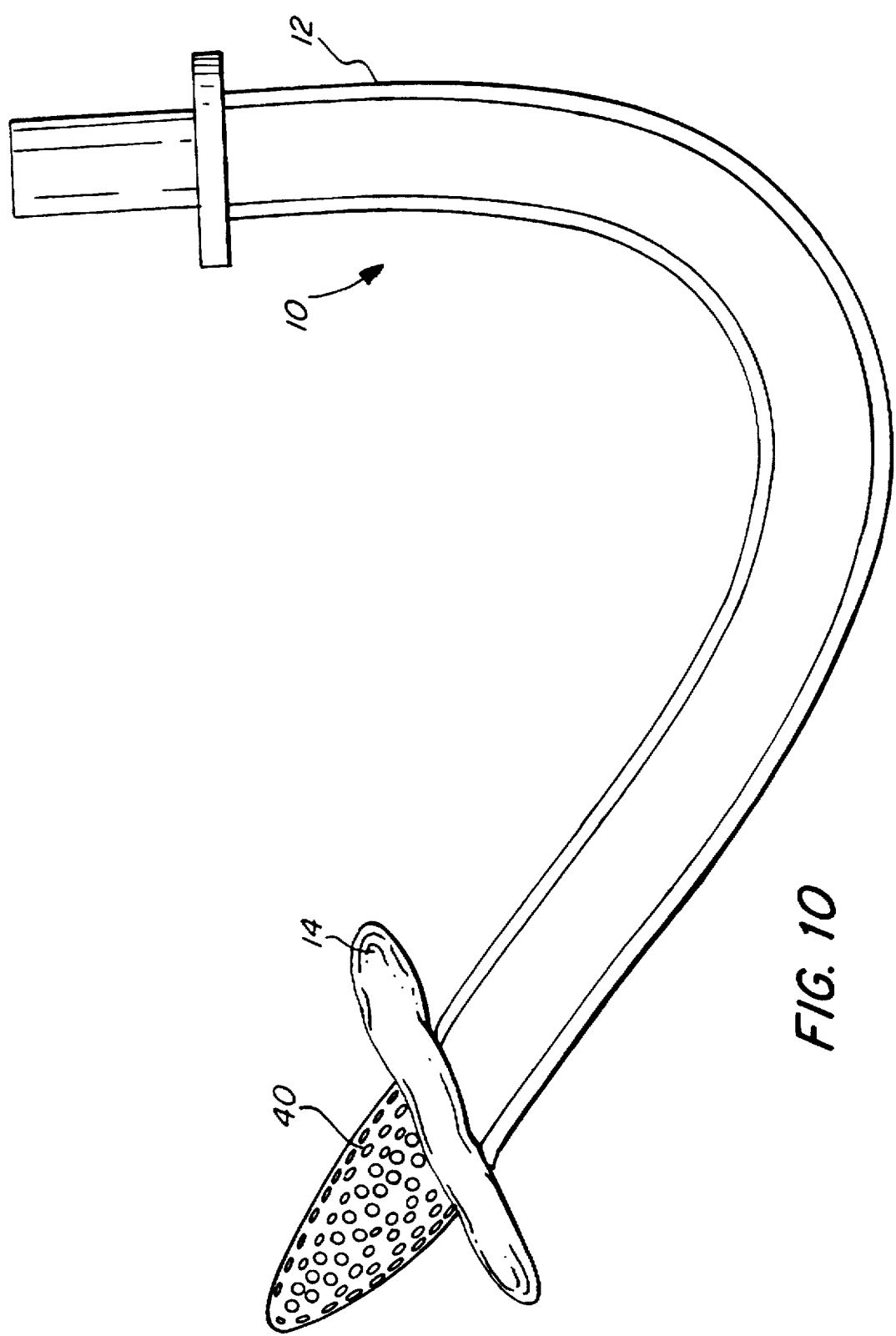
FIG. 10 is a perspective/cutaway view of an oropharyngeal stent and laryngeal aditus shield in accordance with another embodiment of the invention, with a perforated tip section.
Figure 11:
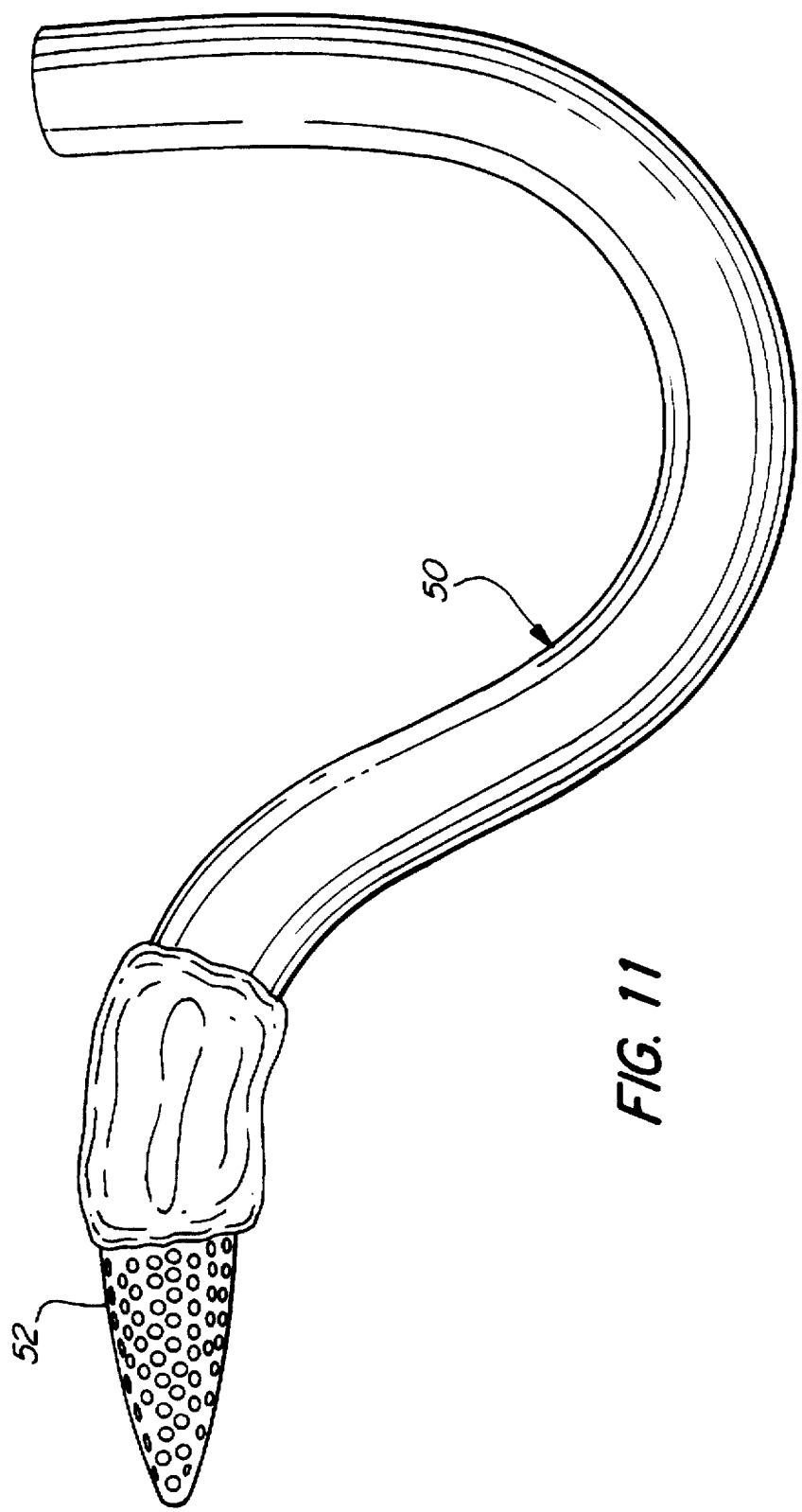
FIG. 11 describes another embodiment of the claimed invention.

Referring to FIG. 10, another embodiment of the oropharyngeal stent 10 in accordance with the invention includes an additional tip section 40 which preferably comprises a perforated tapered shape. Tip section 40 is useful in cases of periglottic obstruction body as only a portion of the tip section 40 need pass through the vocal cords to institute ventilation. In a further alternative embodiment in FIG. 11, a flexible plastic tube 50 is provided that fits inside the airway 16 of stent 10 of FIG. 2. Tube 50 is provided with a tapered perforated tip section 52. Tube 50 may be passed through stent 10 once it is established in the patient and advanced to the tracheal vestibule to pass through the vocal cords. Tip section 52 is useful in cases of periglottic obstruction body as only a portion of the tip section 52 need pass through the vocal cords to institute ventilation.

Figure 8:
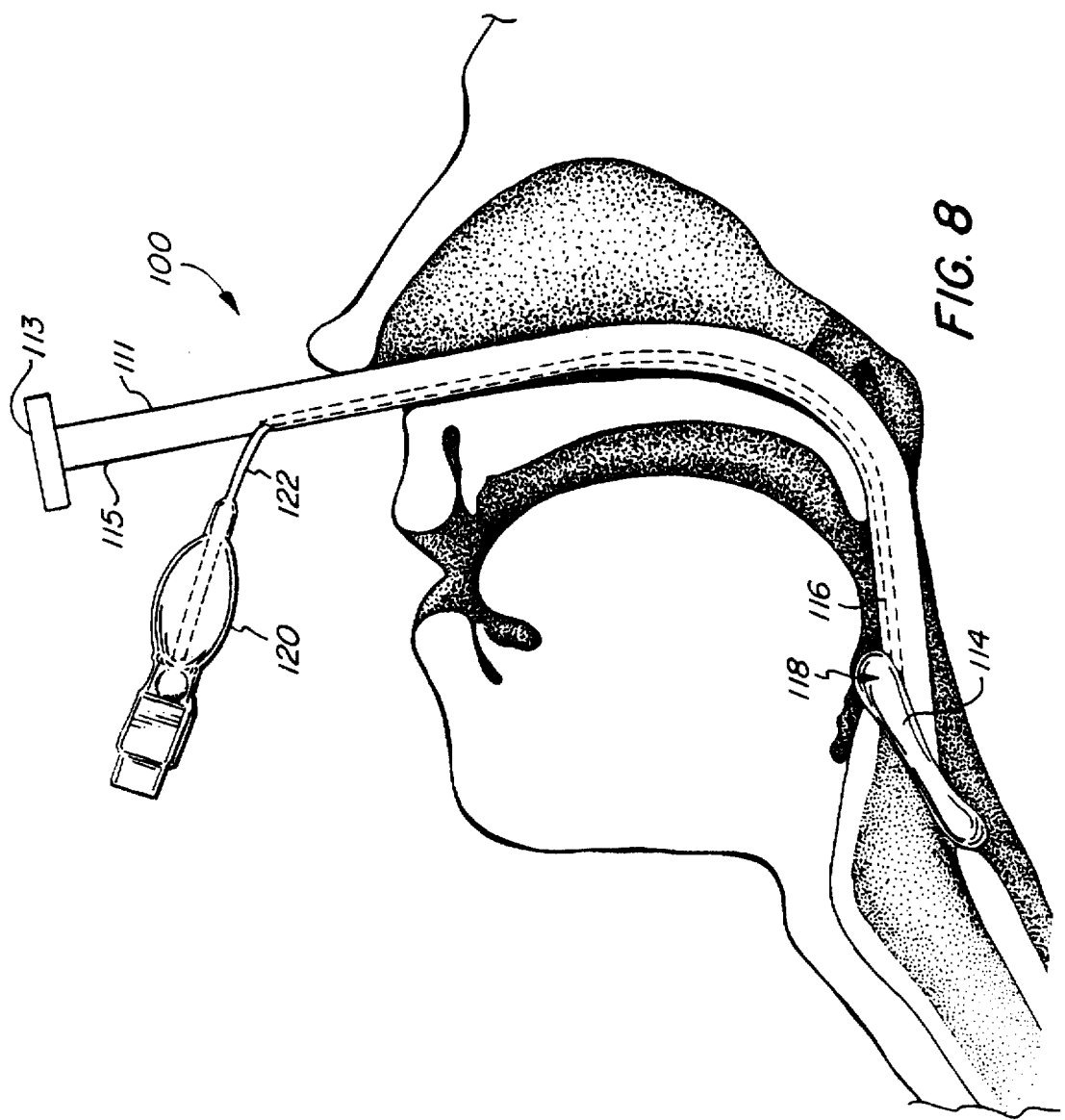
FIG. 8 is a side elevation view with partial cutaway view showing a nasal stent and laryngeal aditus shield, with its cuff deflated, introduced into a patient.
Figure 9:
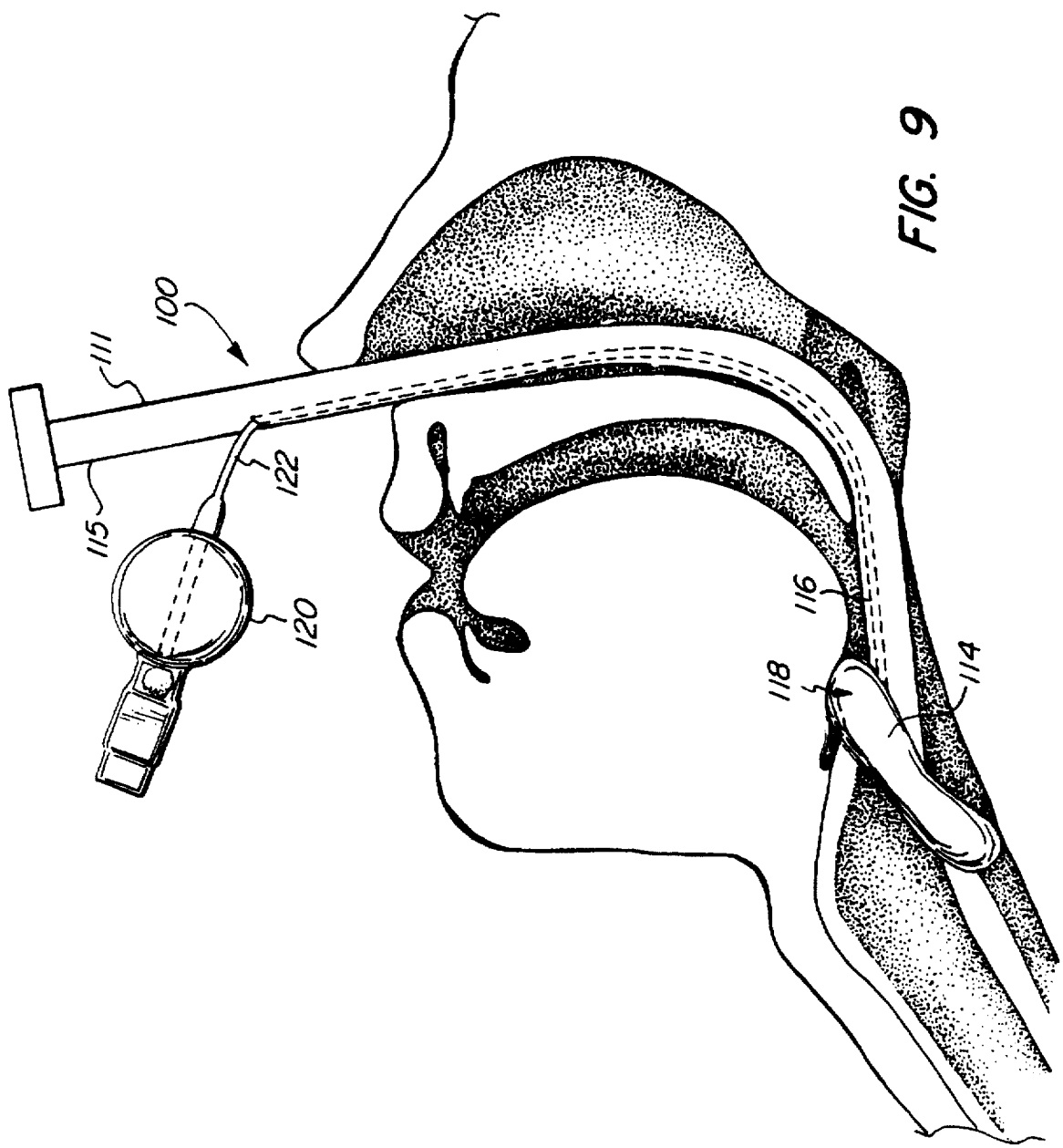
FIG. 9 is a side elevation view with partial cutaway view showing the nasal airway and laryngeal aditus shield of FIG. 8, with its cuff inflated, introduced into a patient.

Referring to the attached FIGS. 8–9, a nasal airway 100 comprises a flexible tubular body 111 curved in shape to conform to the normal anatomy of the human pharynx. Body 111 has a central airway 113 and a proximal end 115 and a distal end 116. Body 111 is preferably formed of a relatively soft, flexible and pliable plastic material. At the distal end of body 111 is provided a laryngeal aditus shield 118. The laryngeal aditus shield 118 comprises an inflatable cuff 114. Cuff 114 is generally triangular in shape (as defined above in connection with second cuff 14) to conform to the cross-sectional shape of the vestibule of the larynx and is sized to fill the area above the vocal cords of a patient but not to overflow into the hypopharynx of the patient. Means for inflating the cuff 114 are provided and preferably includes a conventional valved pilot balloon 120 and tubing 122. Other means may be provided that incorporates the necessary valving and low pressure air or nitrogen.

The method of providing a patent airway using the nasal airway 100 includes introduction of the airway 100 through the nasal passage. After the airway 100 is inserted, the cuff 114 is inflated to seal the area around the larynx.

It is to be appreciated that the foregoing is illustrative and not limiting of the invention, and that various changes and modifications to the preferred embodiments described above will be apparent to those skilled in the art. Such changes and modifications can be made without departing from the spirit and scope of the present invention, and it is therefore intended that such changes and modifications be covered by the following claims.

I claim:

1. An oropharyngeal stent and laryngeal aditus shield comprising:

a flexible tubular body containing a central airway, said body being capable of conforming to a normal anatomy of a human pharynx, said body having a proximal end and a distal end, said distal end being generally triangular in cross-sectional shape while the remainder of said body is generally oval in cross-sectional shape, said body including a tapered tip section at said distal end, said tip section having a plurality of openings for allowing ventilation;

a first inflatable cuff surrounding a portion of said body, said first cuff surrounding said body from the near proximal end thereof to near said distal end thereof, so as not to contact a patient's epiglottis when said oropharyngeal stent and laryngeal aditus shield are established in a patient;

means for inflating said first cuff;

a laryngeal aditus shield comprising a second inflatable cuff located at said distal end of said body, said second cuff being generally triangular in shape to conform to the cross-sectional shape of a vestibule of a larynx and sized to extend from an epiglottis to arytenoids to fill an area above the vocal cords of a patient without lying against an upper end of an esophagus of a patient; and means for inflating said second cuff.

2. An oropharyngeal stent and laryngeal aditus shield in accordance with claim 1 wherein said body further comprises an anterior loop near said distal end of said body between said first and second cuffs.

3. An oropharyngeal stent and laryngeal aditus shield in accordance with claim 1, further comprising an introducer fitted into said body, said introducer comprising a relatively stiff tube shaped to conform to a normal human anatomy of a pharynx.

4. A nasal airway and laryngeal aditus shield comprising:

a flexible tubular body containing a central airway, said body being capable of conforming to a normal anatomy of a human pharynx, said body having a proximal end and a distal end, said distal end being generally triangular in cross-sectional shape while the remainder of said body is generally oval in cross-sectional shape, said body including a tapered tip section at said distal end, said tip section having a plurality of openings for allowing ventilation;

a laryngeal aditus shield comprising an inflatable cuff fixed at said distal end of said body, said cuff being generally triangular in shape to conform to a cross-sectional shape of a vestibule of a larynx and sized to fill an area above vocal cords of a patient without lying against an upper end of an esophagus of a patient; and means for inflating said cuff.

* * * * *